United States Patent [19]

Enderle et al.

[11] Patent Number: 5,078,725
[45] Date of Patent: Jan. 7, 1992

[54] BALLOON CATHETER AND TECHNIQUES FOR DILATING OBSTRUCTED LUMENS AND OTHER LUMINAL PROCEDURES

[75] Inventors: Joyce A. Enderle, Somerville; Andy H. Levine, Boston; John M. Leventhal, Wellesley Hills, all of Mass.

[73] Assignee: C. R. Bard, Inc., Murray Hill, N.J.

[21] Appl. No.: 434,102

[22] Filed: Nov. 9, 1989

[51] Int. Cl.$^5$ ............................................. A61M 29/02
[52] U.S. Cl. .................................... 606/193; 604/96
[58] Field of Search ........................ 604/93, 96–103, 604/282; 606/191, 197, 199

[56] References Cited

U.S. PATENT DOCUMENTS

| | | | |
|---|---|---|---|
| 2,268,321 | 12/1941 | Flynn | 604/282 X |
| 2,308,484 | 1/1943 | Auzin et al. | 18/58 |
| 2,832,343 | 4/1958 | Mose | 606/191 X |
| 4,018,230 | 4/1977 | Ochiai et al. | 606/193 |
| 4,018,231 | 4/1977 | Wallace | 604/101 X |
| 4,413,989 | 11/1983 | Schjeldahl et al. | 604/96 |
| 4,630,609 | 12/1986 | Chin | 128/344 |
| 4,689,041 | 8/1987 | Corday et al. | 604/53 |
| 4,771,777 | 9/1988 | Horzewski et al. | 604/101 X |
| 4,777,951 | 10/1988 | Cribier et al. | 128/344 |
| 4,793,359 | 12/1988 | Sharrow | 128/658 |
| 4,823,805 | 4/1989 | Wojcik | 128/736 |
| 4,898,577 | 2/1990 | Badger et al. | 604/53 |
| 4,927,412 | 5/1990 | Menasche | 604/96 |
| 4,932,956 | 6/1990 | Reddy et al. | 606/192 |
| 4,943,278 | 7/1990 | Euteneuer et al. | 604/96 |

Primary Examiner—John D. Yasko
Assistant Examiner—Adam J. Cermak
Attorney, Agent, or Firm—Wolf, Greenfield & Sacks

[57] ABSTRACT

A balloon catheter for dilating an obstructed lumen in the human body has a specially shaped balloon which, when inflated, has a proximal end cone having a relatively small cone angle and a distal end cone with a relatively large cone angle. The catheter is used in a procedure in which it is inserted into the obstructed lumen, with the balloon in the deflated condition and with the balloon advanced through and past the obstructed region. The balloon then is inflated and then is drawn back through the constricted region to dilate it progressively by the proximal cone of the balloon. Also disclosed are improved techniques relating to use of balloon catheters in the treatment of fallopian tube disorders including procedures for treating hydrosalpinx, for tubal manipulation and for GIFT procedures.

4 Claims, 2 Drawing Sheets

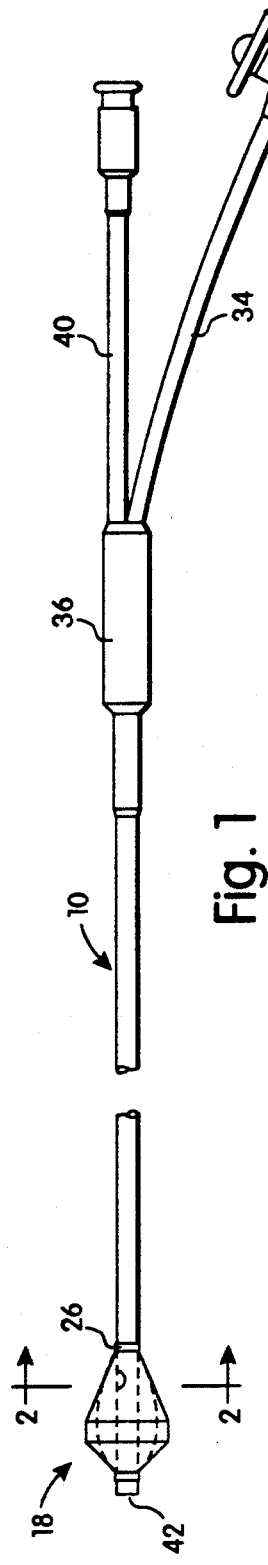
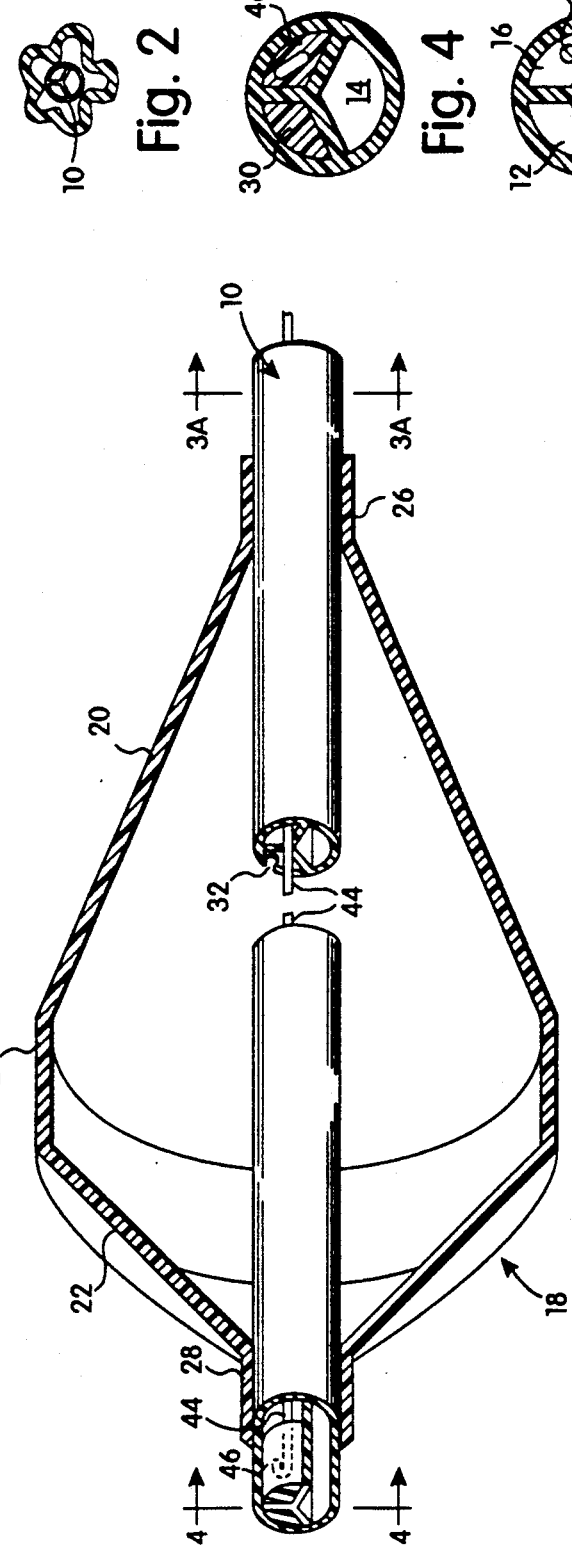
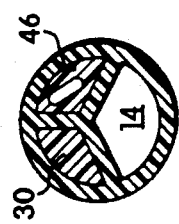
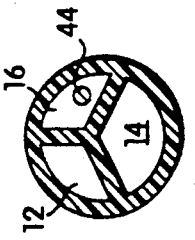
Fig. 1
Fig. 2
Fig. 3
Fig. 3A
Fig. 4

BALLOON CATHETER AND TECHNIQUES FOR DILATING OBSTRUCTED LUMENS AND OTHER LUMINAL PROCEDURES

FIELD OF THE INVENTION

This invention relates to dilation of an obstructed lumen in a human body and to devices and techniques therefor. It also relates to the use of a balloon catheter to perform additional procedures relating to body lumens in general and specifically to procedures involving the fallopian tubes.

BACKGROUND OF THE INVENTION

The obstruction of any of numerous lumens in the human body is a common ailment requiring a variety of medical surgical treatments to correct the condition. For example, obstructions in the fallopian tubes of a female's reproductive system or in the bile duct of the gastrointestinal system are but two of such conditions. A major cause of infertility in woman is distal fallopian tube disease in which the inner surface or the outside of the fallopian tube develops lesions which partially or completely obstruct the lumen through the fallopian tube. A typical treatment for fallopian tube obstruction involves a surgical procedure either through a laparoscope or a more extensive laparotomy in order to excise the lesions. The procedure involves accessing the distal end of the fallopian tube and inserting a forceps in the distal end of the tube. The forceps then is expanded and, in the expanded condition, is withdrawn through the tube. The procedure is repeated a number of times with the forceps being rotated each time to a slightly different angular position in an effort to define a uniform widened opening. The procedure requires a high degree of care and is time consuming. Often it results in bleeding and the development of scar tissue. Nothwithstanding the difficulties in the procedure, it has been widely practiced for many years. It is among the general objects of the invention to provide a novel catheter and new and improved techniques for treating an obstructed lumen, such as, for example only, a fallopian tube, bile duct or the like.

Also among the difficulties encountered in connection with fallopian tube disorders is the treatment of hydrosalpinx, a condition in which the distal end of the fallopian tube becomes completely obstructed and the fallopian tube fills with fluid. In the treatment of hydrosalpinx, it is necessary to surgically reconstruct the opening at the distal end, by surgically forming several longitudinal slits in the distal end of the fallopian tube and then everting the flaps defined between the slits to redefine a distal fallopian opening. Such a procedure typically has required one or more assistants for the physician in order to hold the portions of the fallopian tube while the incisions are made and the everting procedure is performed. The procedure is difficult in that it requires delicate cooperation between the physician and his assistants. The procedure typically has presented considerable risk of trauma to the fallopian tube. It is among the objects of the invention to provide an improved technique in which a balloon catheter is used to engage and stabilize the fallopian tube while the distal end of the fallopian tube is cut and everted. Additionally, it is also among the general objects of the invention to provide a technique for using a balloon catheter to securely engage the fallopian tube to permit tubal manipulation to expose and facilitate treatment of portions of the fallopian tube.

SUMMARY OF THE INVENTION

One aspect of the invention involves the use of a special balloon catheter that is inserted into the lumen on one side of the obstruction, with the balloon in a collapsed condition. The balloon is advanced through the obstruction to a location distally of the obstruction. The balloon then is inflated and, while maintained in an inflated condition, is drawn proximally through the lumen to effect a progressive dilation along the length of the lumen and through the obstruction.

The catheter includes an elongate flexible shaft and a balloon at its distal end. The balloon has a proximal end cone which defines a relatively shallow sloping, relatively small conical angle and a more steeply sloped, larger conical angle distal cone. The distal cone defines a relatively blunt distal end for the catheter. The balloon may have a cylindrical midportion between the cones. The gradual slope of the proximal cone is effective to progressively and gradually dilate the lumen and the obstruction as the catheter is drawn through the lumen. The balloon is formed from a relatively inelastic material such as polyethylene terephthalate and is flexible to facilitate its collapse and inflation. The size and specific configuration for the balloon may be selected for the particular procedure and patient. The relatively blunt distal end of the balloon, and the close location of the distal end of the balloon to the distal end of the catheter shaft results in a minimal distal extension for the catheter so as to reduce interference with deep insertion of the device.

In another aspect of the invention, when provided with a cylindrical central section, the balloon also may be used to provide a stable base within a tubular organ, to support that organ while performing a surgical procedure on the organ. For example, a balloon catheter in which the balloon has a cylindrical central section may be inserted into an opening formed in the distal end of a fallopian tube having a hydrosalpinx condition. The balloon is inflated in the distal end of the fallopian tube so that the cylindrical central section engages firmly the fallopian tube and provides a means by which the fallopian tube may be held in a stable position while incisions are made in the distal end of the fallopian tube to reform an opening.

In a further aspect of the invention, a balloon catheter may be inserted into the distal opening in the distal end of the fallopian tube and inflated to securely engage the distal end of the fallopian tube. So engaged, the catheter enables manipulation of the fallopian tube to expose selected regions of the tube and enable those regions to be treated, for example, as to remove peritubal adhesions.

It is among the general objects of the invention to provide a new and improved device and technique for dilating obstructed lumens in the human body.

Another object of the invention is to provide a new and improved technique for dilating a obstructed lumen by drawing a tapered balloon through the obstruction.

A further object of the invention is to provide a new balloon catheter for dynamic dilation of an obstructed lumen in which the balloon is provided with a proximal cone having a gradual taper and a distal cone having an abrupt taper.

Another object of the invention is to provide a catheter and a technique for its use that reduces the trauma and complexity attended to dilation of fallopian tubes and other lumens in the human body.

A further object of the invention is to provide a technique for using a balloon catheter in the treatment of a fallopian tube having a hydrosalpinx condition as well as for tubal manipulation.

DESCRIPTION OF THE DRAWINGS

The foregoing and other objects and advantages of the invention will be appreciated more fully from the following further description thereof with reference to the accompanying drawings wherein:

FIG. 1 is a fragmented illustration of the catheter;

FIG. 2 is a cross-section of the catheter as seen along the line 2—2 of FIG. 1 with the balloon in a collapsed condition;

FIG. 3 is an enlarged longitudinal sectional illustration of the balloon end of the catheter;

FIG. 3A is a sectional illustration of the catheter shaft as seen along the line 3A—3A of FIG. 3;

FIG. 4 is a sectional illustration through the catheter as seen along the line 4—4 of FIG. 3;

DESCRIPTION OF THE PREFERRED EMBODIMENT

Figure 5:
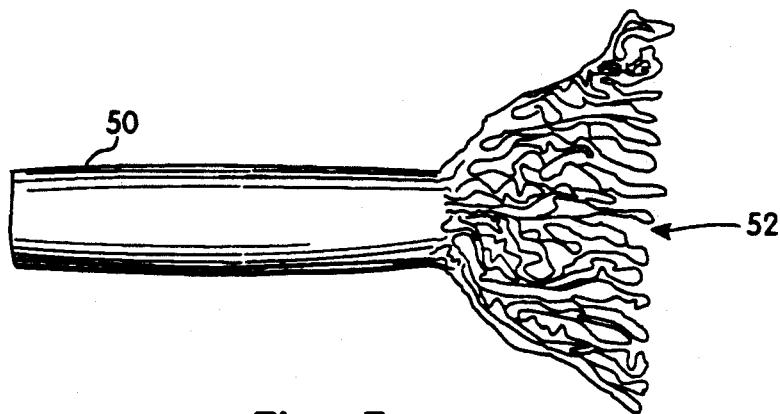
FIG. 5 is an illustration of the distal, fimbria end of a fallopian tube.

As shown in FIG. 1, the catheter includes an elongate flexible shaft 10 having a proximal end, seen to the right in FIG. 1 and a distal end, seen to the left in FIG. 1. The shaft is flexible and may be formed, as by extrusion, from an appropriate plastic material such as a urethane material. The shaft has at least one, and may have two or more lumens, extending longitudinally through the shaft, as indicated at 12, 14, 16 in FIG. 3A.

A flexible balloon, indicated generally at 18, is mounted at the distal end of the catheter. The balloon is inflatable and deflatable as will be described. The balloon 18 is formed preferably from a relatively inelastic material, such as polyethylene terephthalate. The balloon may be manufactured as described in U.S. Pat. No. 4,490,421 (Levy). The balloon is formed to include a proximal cone section 20 and a distal cone section 22 with an intermediate cylindrical section 24. The proximal end of the proximal cone terminates in a cylindrical collar 26 and the distal end of the distal cone 22 terminates in a distal collar 28. The balloon is attached to the catheter shaft 10 by adhesively attaching the collars 26, 28 to the shaft. One of the lumens, such as lumen 12 is used for inflating and deflating the balloon. The lumen is plugged at its distal end as indicated at 30 in FIG. 4. An opening 32 is formed in the shaft within the balloon 18 to communicate the inflation lumen 12 with the interior of the balloon. An inflation medium, such as an appropriate liquid is used to inflate and deflate the balloon and is communicated with the lumen 12 through a flexible side tube 34 at the proximal end of the catheter. The side tube 34 is attached to the catheter at a Y-fitting molding 36 which may be molded to the proximal end of the shaft 10. A stopcock 38 preferably is attached to the proximal end of the side tube 34. Another tube 40 may be connected at the Y-fitting molding 36 to be in communication with another of the lumens, such as lumen 14. Lumen 14 may extend fully through the catheter shaft and be open at the distal tip of the catheter, at a distal outlet orifice 42. The lumen 14 may be used to infuse or aspirate liquid through the catheter as may be desired by the physician. The lumen 14 also may be used to receive a guidewire or another smaller catheter should that be desirable in a particular procedure.

It is desirable that the balloon be able to collapse to a relatively low profile, that is, to have a relatively small effective diameter when the balloon is collapsed. To that end, the balloon preferably is formed so that when it is collapsed, by applying negative pressure to the balloon lumen, the balloon will tend to collapse in a pleated configuration as suggested in FIG. 2. The balloon may be manufactured by a process that will cause the balloon to tend to collapse into the pleated configuration. In that process, after the balloon has been formed as described in U.S. Pat. No. 4,490,421, the balloon then is tensioned by its ends until it forms a plurality of pleats while under tension. While maintaining the balloon under tension, the balloon first is heated and then cooled. The tension then may be released and the balloon thereafter will tend to assume the pleated configuration when it is collapsed. The process for forming the pleats is described in further detail in U.S. patent application Ser. No. 291,566, filed Dec. 29, 1988 to which reference is made and which is hereby incorporated by reference.

As shown in further detail in FIGS. 3 and 3A, a stiffener 44 is provided within the distal end of the catheter in the region of the balloon 18. The stiffener may be attached at its distal end by embedding it in a plug 46 in the distal end of the lumen 16. The stiffener may extend proximally of the order of about 10 cm. By way of example, the stiffener may have a distal segment about 3 cm long of the order of about 0.016" in diameter. The proximal 7 cm may be tapered to a diameter of the order of 0.005". The stiffener extends fully beyond the length of the balloon. It serves to reduce the degree of bowing of the catheter shaft in the region of the balloon as the balloon is inflated. The use of a pleated balloon without the stiffener may otherwise result in a sharply bowed, possibly kinked, shaft in the region of the balloon.

FIG. 5 illustrates the distal portion of a fallopian tube 50 in which a portion of the tube has a constriction. Typically, the fallopian tube is about 10–11 long and has an internal lumen of the order of 8 to 9 mm in diameter at its distal end. In a healthy fallopian tube, the distal end has a plurality of fimbria 52 which facilitate collection of the ovum to guide the ovum into the passageway of the fallopian tube so that the ovum may travel along the fallopian tube toward the uterus. The other end of the fallopian tube is connected to the uterus by a progressively narrowing passageway. By way of example, in a typical fallopian tube the passageway may reduce in size to only a 1 to 3 mm diameter opening.

Figure 6:
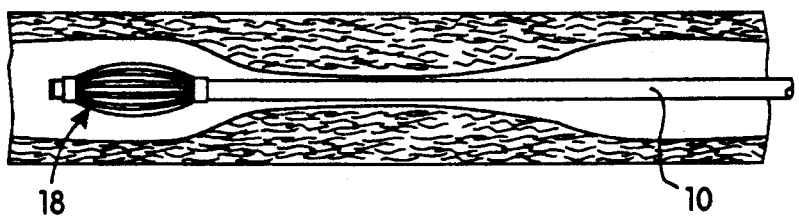
FIG. 6 is a highly diagrammatic illustration of the catheter having been inserted into and through an obstructed region of the fallopian tube.
Figure 7:
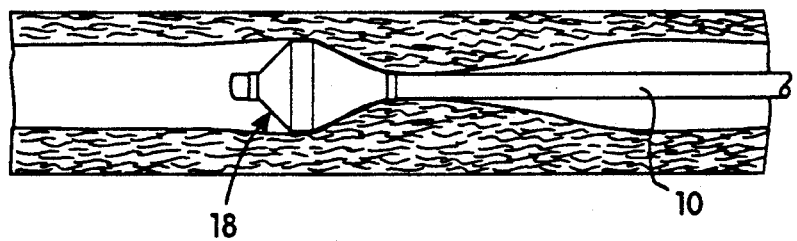
FIG. 7 is a highly diagrammatic illustration of the catheter as it is withdrawn through the fallopian tube to progressively dilate the obstruction.

FIGS. 6 and 7 illustrate, diagrammatically, the manner in which the balloon catheter of the present invention is used to enlarge the passageway in a stenosed or constricted distal portion of the fallopian tube. The physician obtains access to the distal fimbria end of the fallopian tube either through a laparoscope or by performing a more extensive laparotomy. The physician must determine whether the entrance to the fallopian tube is open and, if not, he may make an incision to permit entry. The catheter, in accordance with the invention, then is collapsed by aspiration through the inflation/deflation lumen. With the balloon collapsed in a low profile configuration, e.g., see FIG. 2, it is inserted through the fimbria end of the fallopian tube and is advanced to and through the obstruction, to locate the balloon beyond the obstruction The balloon then is inflated, preferably with liquid such as saline. The balloon is dimensioned so that its inflated diameter corresponds to the normal unobstructed diameter of the lumen in the fallopian tube. Of course, when the invention is used with other body lumens, the diameter of the balloon should be selected appropriately. After the balloon is inflated, the catheter is pulled back toward the distal end of the fallopian tube to cause the proximal cone 20 of the balloon to be drawn through the constriction. The proximal cone 20 of the balloon is provided with a relatively gradual taper, defining a relatively small cone angle, so that the conical configuration will progressively act as a wedge to dilate progressively the constricted region as the catheter is pulled through the constricted region. Thus, by drawing the balloon through the constriction, the constriction is dilated.

It should be noted that the distal cone 22 is shorter and has a larger cone angle than the proximal cone 20. It is desirable to have a shorter distal cone in order that the distal end of the catheter does not interfere with deep placement of the balloon of the catheter.

In some cases, the fimbria have degenerated, the opening to the fallopian tube may be completely blocked and the physician may determine that it is best to surgically reconfigure the end of the fallopian tube. The configuration of the balloon of the present invention facilitates such a procedure. After making an incision in the end of the fallopian tube so that the balloon can be inserted into the tube, the balloon is inserted and inflated. The inflated balloon, and particularly the cylindrical portion 24 serves to hold the fallopian tube securely and provides a stable platform on which the surgery may be performed.

By way of example, in the illustrative embodiment which is intended to be used to dilate a constricted fallopian tube, the proximal cone 20 may have an angle of the order of 25° while the cone angle of the distal cone may be of the order of 46°. The balloon is about 2.5 cm long, with the proximal cone being approximately 1.4 cm long, the central cylindrical section being approximately 0.5 cm long and the distal cone being approximately 0.6 cm long. The diameter of the balloon, in the cylindrical segment, is 15 mm.

In other aspects of the invention, a balloon catheter may be inserted into the distal end of a fallopian tube for a number of purposes and in connection with several treatments for fallopian tube-related conditions. It often is necessary in the treatment of fallopian tube conditions, to be able to hold and manipulate the fallopian tube to expose various portions of the tube in order that those portions may be treated. For example, a fallopian tube having peritubal adhesions will require that the tube be manipulated to expose those adhesions to an appropriate surgical instrument, such as a laser energy delivery device, in order to remove the adhesions. Holding and manipulating the fallopian tube is a difficult procedure. Typically, it has involved several surgical personnel each holding a portion of the fallopian tube and requiring unison manipulation of the tube to expose the desired portions to the surgical instrument. A balloon catheter, however, may be used to reduce considerably the awkwardness and difficulty previously presented in tubal manipulation. Thus, a balloon catheter may be inserted into the distal end of the fallopian tube and may be inflated firmly into engagement with the inner lumen of the tube. Once so inflated, it engages firmly the fallopian tube and facilitates manipulation of the fallopian tube by simple manipulation of the catheter shaft. The physician may perform the required manipulations himself with one hand while using the other hand to guide the surgical instrument.

In a further technique, a balloon catheter having a central lumen 14 may be used in a gamete intra fallopian transfer (GIFT) in which eggs and sperm are inserted together into a patient's fallopian tube. In such procedure, it is necessary to hold the fallopian tube steady while a transfer catheter carrying the eggs and sperm is inserted into the fallopian tube. Here, again, the technique for holding the fallopian tube steady has required the use of several surgical personnel, each holding a portion of the fallopian tube with a forcep. In accordance with the present invention, a balloon catheter having a central lumen, such as the lumen 14, extending fully to the distal end of the catheter may be inserted into the fallopian tube and inflated. Once inflated, the fallopian tube is secured in position with respect to the catheter. A smaller transfer catheter then may be passed through the central lumen in the balloon catheter. Thus, the balloon catheter serves the dual purpose of holding the fallopian tube steady while providing a direct path for the transfer catheter into the fallopian tube. The GIFT procedure thus is greatly simplified.

Thus, from the foregoing, it will be appreciated that the invention provides a means by which the procedure for enlarging a constricted passage in a body lumen, such as a fallopian tube, is simplified and may be achieved with less difficulty than with prior techniques. The invention provides a new catheter configuration and method for enlarging constricted body lumens. Additionally, in other aspects of the invention, balloon catheters may be used to facilitate various treatments of fallopian tube conditions and procedures in a manner that simplifies those procedures and enhances their effectiveness. It should be understood, however, that the foregoing description of the invention is intended merely to be illustrative thereof and that other modifications and embodiments may be apparent those skilled in the art without departing from its spirit.

Having thus described the invention what we desire to claim and secure by Letters Patent is:

1. A dilation catheter comprising:
   an elongate flexible tubular shaft having a proximal end and a distal end;
   a balloon formed from a relatively inelastic flexible material mounted to the distal end of the shaft, the balloon having a proximal cone and a distal cone, the ends of the cones being attached to the shaft, the proximal cone being exposed so as to be directly engageable with the portion of a patient's body, the proximal cone defining a smaller conical angle than the distal cone;
   the balloon having an untapered cylindrical section between the proximal and distal cones;
   an inflation lumen extending through the catheter shaft and being in communication with the interior of the balloon; and
   the length of the proximal cone measured lengthwise of the shaft being greater than the combined similarly measured length of the distal cone and cylindrical section.

2. A catheter as defined in claim 1 wherein the balloon length is approximately equal to the maximum inflated diameter of the balloon.

3. A dilatation catheter comprising:
an elongate flexible tubular shaft having a proximal end and a distal end;
a balloon formed from a relatively inelastic flexible material mounted to the distal end of the shaft, the balloon having a proximal cone and a distal cone, the ends of the cones being attached to the shaft, the proximal cone being exposed so as to be directly engageable with a portion of a patient's body, the proximal cone defining a smaller conical angle than the distal cone;
the balloon being formed to include a plurality of longitudinal pleats when the balloon is in a deflated condition; and
a stiffener extending through the shaft of the catheter in the region of the balloon, the stiffener being attached at its distal end to the shaft and being free at its proximal end.

4. A dilation catheter as defined in any one of claims 1, 2 or 3 wherein the distal cone is located in close proximity to the distal end of the shaft.

* * * * *